United States Patent [19]
Albrecht et al.

[11] Patent Number: 4,929,752
[45] Date of Patent: May 29, 1990

[54] PROCESS FOR THE PREPARATION OF 1-AMINE-2-NAPHTHOL-4-SULFONIC ACID

[75] Inventors: Bernhard Albrecht, Buus, Switzerland; Jürgen Beyrich, Huttingen, Fed. Rep. of Germany

[73] Assignee: Ciba-Geigy Corporation, Ardsley, N.Y.

[21] Appl. No.: 352,652

[22] Filed: May 12, 1989

Related U.S. Application Data

[63] Continuation of Ser. No. 95,727, Sep. 14, 1987, abandoned.

[30] Foreign Application Priority Data

Sep. 23, 1986 [CH] Switzerland ............... 3794/86

[51] Int. Cl.$^5$ ............................................. C07C 143/66
[52] U.S. Cl. ......................................................... 562/70
[58] Field of Search ........................................... 562/70

[56] References Cited

FOREIGN PATENT DOCUMENTS 174519 8/1985 European Pat. Off. .
3431695 3/1986 Fed. Rep. of Germany ...... 260/509

OTHER PUBLICATIONS

Nerad et al., C.A., 86-155,397j (1977).
Organic Synth. vol. I (1941) pp. 411–413.
Bios Final Report No. 986 Pt. 1, Item No. 22, pp. 44–45 & pp. 146–147.

*Primary Examiner*—Nicky Chan
*Attorney, Agent, or Firm*—Kevin T. Mansfield

[57] ABSTRACT

There is disclosed an improved semi-continuous and continuous process for the preparation of 1-amino-2-naphthol-4-sulfonic acid by nitrosation of 2-naphthol, addition of bisulfite, acidification with mineral acid and reduction of the reaction product so obtained, which comprises charging the reactor with the nitrosating agent and simultaneously adding 2-naphthol and mineral acid simultaneously in separate streams in the semi-continuous process, or charging the reactor with the reaction mass and simultaneously adding 2-naphthol, mineral acid and the nitrosating agent in separate streams in the continuous process. The product can be further used, without isolation, for the synthesis of dyes.

9 Claims, No Drawings

PROCESS FOR THE PREPARATION OF 1-AMINE-2-NAPHTHOL-4-SULFONIC ACID

This application is a continuation, of application Ser. No. 095,727, filed 9/14/87, now abandoned.

The present invention relates to a novel semi-continuous and continuous process for the preparation of 1-amino-2-naphthol-4-sulfonic acid by the simultaneous addition of a finely dispersed aqueous suspension of 2-naphthol and sulfuric acid, in separate streams, to a nitrosating agent charged to the reactor in the semi-continous process, or by the simultaneous addition of 2-naphthol, mineral acid and nitrosating agent, in separate streams, to a reaction mass charged to the reactor in the continuous process.

1-Amino-2-naphthol-4-sulfonic acid is an important intermediate for the synthesis of dyes, especially acid metal complex dyes. Many processes for the preparation of this compound are therefore known. Attention is drawn e.g. to Organic Synthesis, Vol. I (1941), page 411, and Vol. II (1943), page 42. According to this procedure, the reaction of 2-naphthol with sodium nitrite is carried out in a dilute aqueous solution, and the isolated paste of nitrosated 2-naphthol is reacted with the 2.7-fold molar amount of sodium bisulfite. After acidification with sulfuric acid, the product is isolated. According to the BIOS Final Report No. 986, Pt. 1, Item No. 22, pp. 44–45 and 146–147, 1-amino-2-naphthol-4-sulfonic acid is prepared in aqueous solution. This process, however, gives rise to the formation of large amounts of sodium sulfate which contaminate the wastewater. The shortcomings of all these processes is that they have to be carried out in very dilute solutions and that large amounts of sodium bisulfite are required.

Finally, German Offenlegungsschrift 3 431 695 discloses a process for the preparation of 1-amino-2-naphthol-4-sulfonic acid by nitrosation of 2-naphthol, addition of bisulfite and acidification with a mineral acid, which process comprises carrying out the nitrosation in the presence of a water-miscible organic solvent. In addition to affording a low space/time yield, this process has the serious disadvantage of polluting the wastewater with organic solvents.

The present invention relates to a process for the preparation of 1-amino-2-naphthol-4-sulfonic acid that overcomes the difficulties referred to above. This process comprises nitrosating 2-naphthol, adding bisulfite, acidifying the reaction mixture with a mineral acid and reducing the reaction product so obtained, said process being carried out in aqueous medium, and either (a) in the continuous process, charging the reactor with the nitrosating agent and adding 2-naphthol and mineral acid simultaneously in separate streams, or (b) in the continuous process, charging the reactor with a reaction mass and adding 2-naphthol, mineral acid and the nitrosating agent simultaneously in separate streams.

The 1-amino-2-naphthol-4-sulfonic acid can be further processed direct, i.e. without being isolated, to dyes such as Eriochrome Black.

The starting materials for this process and the preparation thereof are known.

The starting 2-naphthol is conveniently added in the form of a finely dispersed aqueous suspension or slurry to the nitrosating agent charged to the reactor. Owing to the low solubility of 2-naphthol in the mineral acid, it is advantageous to convert it by crystallisation and wet grinding from an aqueous emulsion into a finely dispersed form. This expedient results in a marked increase in the rate of reaction. The wet grinding is carried out in conventional grinding machines. To achieve a stable dispersion, grinding can be carried out in the presence of a dispersant, e.g. sulfite cellulose lye (Netzöl®) or Turkey-red oil, and of an organic water-miscible organic solvent, e.g. an alcohol.

The process is conveniently carried out by adding 2-naphthol and the mineral acid in a ratio such that 1 to 1.1 moles of mineral acid are supplied per 1 mole of 2-naphthol.

Preferred nitrosating agents in the process of this invention are alkali metal nitrites or alkaline earth metal nitrites as well as organic nitrites such as glycol nitrites. The most preferred nitrosating agent is sodium nitrite.

The preferred mineral acid is a hydrohalic acid such as hydrochloric acid, phosphoric acid, phosphonic acid, phosphorous acid and, in particular, sulfuric acid. The mineral acid will normally be one having a concentration of 5 to 95% by weight, preferably of 25 to 50% by weight.

The bisulfite capable of addition to the nitrosonaphthol is e.g. an alkali metal sulfite, an alkaline earth metal sulfite or an ammonium sulfite. The preferred bisulfite is sodium bisulfite.

The semi-continous process is carried out e.g. by adding 2-naphthol in the form of an aqueous, finely dispersed suspension having a particle size preferably smaller than 50 μm, most preferably 1 to 10 μm, and the mineral acid, preferably 35% aqueous sulfuric acid, simultaneously in separate streams to a mixture that contains aqueous sodium nitrite solution, any residual reaction mass, a 1-nitroso-2-naphthol from the previous reaction, and ice, and reacting the 2-naphthol to 1-nitroso-2-naphthol in the temperature range from 0° to 10° C., preferably from 0° to 5° C. After stirring until the reaction is complete, the reaction mass is reacted with sodium bisulfite, in the temperature range from 15° to 30° C., to 1-hydroxyl-amino-2-tetralonesulfonic acid, which is then reduced to amino-2-naphthol-4-sulfonic acid in the temperature range from 25° to 90° C. and in the acid pH range, e.g. from 5 to 5.5. If it is desired to isolate this product, then isolation is effected e.g. by filtration, washing and drying, e.g. in a vacuum drier.

The reduction of the hydroxylaminotetralone compound is preferably carried out in the presence of a catalyst, e.g. a transition metal sulfate ($CuSO_4$, $FeSO_4$). The transition metal sulfate can contain water.

The process can be carried out semi-continuously or continuously, utilising a single reactor for all steps.

The process can be illustrated by the following reaction scheme:

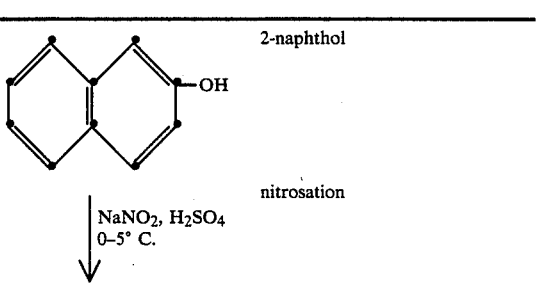

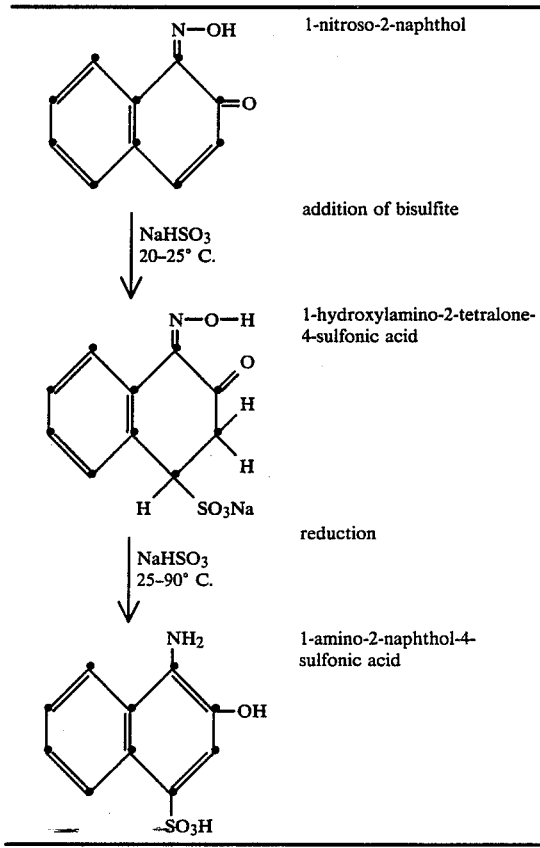

A further advantage of the process of this invention resides in the feature that the 1-amino-2-naphthol-4-sulfonic acid is obtained in high yield and great purity, as the 2-naphthol is nitrosated very rapidly and completely. There is consequently no local accumulation of mineral acid and evolution of nitrose gases in the reaction mixture, so that the formation of by-products is substantially avoided. The concentration of mineral acid thus remains essentially constant at a low level during the reaction.

The invention is illustrated by the following example in which the parts are by weight.

Example 1:
(a) Preparation of the suspension of 2-naphthol-emulsion and grinding
A ball mill is charged with
250 parts of water
4 parts of sulfite cellulose lye powder as dispersant, and
144 parts of 2 naphthol, and the mixture is finely ground.
The resultant liquid suspension is made up to 462 parts with water.
(b) Nitrosation of 2-naphthol
With cooling, a reactor is charged with
500 parts of ice and
72.9 parts of sodium nitrite.
Over the course of 60 minutes
462 parts of the 2-naphthol suspension obtained in (a) and
147 parts of 35% sulfuric acid are added simultaneously and separately, whereupon 1-nitroso-2-naphthol precipitates in the form of coarse crystals.
The reaction mass is then stirred for 1 hour at 5°–10° C.
(c) Addition of bisulfite
To the reaction mass obtained in (b) are added 572 parts of 40% sodium bisulfite solution and the reaction mass is warmed to 25° C.
(d) Reduction
To the reaction mass are added
613 parts of 35% sulfuric acid and
1.15 parts of $CuSO_4 \cdot 5 H_2O$ at 25° C.
When this addition is complete, the reaction mass is heated over 1 hour to c. 85° C. and the 1-amino-2-naphthol-4-sulfonic acid begins to precipitate. The batch is allowed to react for 30 minutes at 85° C.
(e) Filtration
The viscous suspension of 1-amino-2-naphthol-4-sulfonic acid is filtered with suction at 85° C. and the filter cake is washed with several portions of water and the water is subsequently removed under vacuum. The moist filter cake is then dried at 80° C. in a vacuum drier, affording 202.6 parts of 1-amino-2-naphthol-4-sulfonic acid as a white powder.
This corresponds to a yield of 85% (based on naphthol employed).

EXAMPLE 2:

continuous nitrosation
In a reactor with jacket cooling
462 parts/h of a suspension of 2-naphthol (prepared according to (a) in Example 1),
147 parts/h of 35% sulfuric acid, and
182 parts/h of a 40% solution of sodium nitrite are added in separate streams to a residual reaction mass (from the previous batch) and reacted at a temperature of 0°–5° C. and a pH of 2–3. After interrupting the addition, the batch is allowed to react for 30 minutes and then 60% of the reaction mass is removed for further processing in accordance with steps (c) to (e) in Example 1.
The semi-continuous nitrosation can be repeated with the residual reaction mass.

What is claimed is:

1. In a process for the preparation of 1-amino-2-naphthol-4-sulfonic acid by nitrosation of 2-naphthol, addition of bisulfite, acidification with mineral acid and reduction of the reaction product so obtained, the improvement which comprises carrying out said nitrosation of 2-naphthol semi-continuously or continuously in a reaction medium which is free of water-miscible organic solvents and which consists essentially of water, and either (a) in the semi-continuous process, charging the reactor with the nitrosating agent and adding an aqueous suspension of 2-naphthol and mineral acid simultaneously in separate streams, or (b) in the continuous process, charging the reactor with a reaction mass obtained from a previous nitrosation and adding said 2-naphthol suspension, mineral acid and the nitrosating agent simultaneously in separate streams to said reaction mass.

2. A process according to claim 1, wherein the semi-continuous process, comprises adding an aqueous suspension of 2-naphthol and mineral acid simultaneously in separate streams to an aqueous nitrosating medium.

3. A process according to claim 1 wherein the continuous process, comprises adding an aqueous suspension of 2-naphthol, mineral acid and nitrosating agent simultaneously in separate streams to an aqueous reaction mass from a previous nitrosation.

4. A process according to claim 1, which comprises adding 2-naphthol and mineral acid in a ratio such that 1.1 moles of mineral acid are supplied per 1 mole of 2-naphthol.

5. A process according to claim 1, wherein the mineral acid is sulfuric acid.

6. A process according to claim 2, wherein the particle size of the aqueous suspension of 2-naphthol is smaller than 50 μm.

7. A process according to claim 1, wherein the nitrosation is carried out in the temperature range from 0° to 10° C.

8. A process according to claim 7, wherein the nitrosation is carried out in the temperature range from 0° to 5° C.

9. A process according to claim 1, wherein the concentration of mineral acid remains substantially constant during the reaction.

* * * * *